(12) United States Patent
Cuervo

(10) Patent No.: US 11,439,522 B2
(45) Date of Patent: Sep. 13, 2022

(54) VALVE ASSEMBLY FOR A PROSTHETIC SOCKET

(71) Applicant: Fillauer Companies, Inc., Chattanooga, TN (US)

(72) Inventor: Bryan Jeffrey Cuervo, Soddy Daisy, TN (US)

(73) Assignee: Fillauer Companies, Inc., Chattanooga, TN (US)

( * ) Notice: Subject to any disclaimer, the term of this patent is extended or adjusted under 35 U.S.C. 154(b) by 0 days.

(21) Appl. No.: 17/409,685

(22) Filed: Aug. 23, 2021

(65) Prior Publication Data
US 2022/0062013 A1 Mar. 3, 2022

Related U.S. Application Data

(60) Provisional application No. 63/070,245, filed on Aug. 25, 2020.

(51) Int. Cl.
*A61F 2/80* (2006.01)
(52) U.S. Cl.
CPC .......... *A61F 2/80* (2013.01); *A61F 2002/805* (2013.01)
(58) Field of Classification Search
CPC ............................. A61F 2/80; A61F 2002/805
See application file for complete search history.

(56) References Cited

U.S. PATENT DOCUMENTS

| | | | | |
|---|---|---|---|---|
| 5,490,537 A * | 2/1996 | Hill | ..................... | B25B 23/0085 137/315.42 |
| 6,287,345 B1 * | 9/2001 | Slemker | ..................... | A61F 2/80 623/33 |
| 6,334,876 B1 * | 1/2002 | Perkins | ..................... | A61F 2/80 623/34 |
| 7,993,413 B2 * | 8/2011 | Perkins | ..................... | A61F 2/80 251/285 |
| 8,113,235 B2 * | 2/2012 | Bogue | ....................... | A61F 2/78 623/34 |
| 8,999,004 B2 * | 4/2015 | Abu Osman | ............. | A61F 2/78 623/32 |
| 10,639,174 B2 * | 5/2020 | Chabloz | .................... | A61F 2/80 |
| 2002/0143318 A1 * | 10/2002 | Flinchbaugh | ..... | A61M 5/16881 604/179 |
| 2014/0067084 A1 * | 3/2014 | Soss | ......................... | A61F 2/80 623/33 |
| 2016/0120665 A1 * | 5/2016 | Muller | ..................... | A61F 2/80 623/34 |

* cited by examiner

*Primary Examiner* — Bruce E Snow
(74) *Attorney, Agent, or Firm* — Thorpe North & Western LLP

(57) ABSTRACT

A technology is described to allow the controlled ingress and egress of air through a prosthetic socket by the insertion of a mechanical valve. The air flow through the valve is controlled by a toggle switch that moves a magnet to shift the position of a valve stem or valve obstruction in the valve. The normal, or closed, position allows flow out of the socket for donning and walking. The open position allows for free flow of air for donning or doffing.

21 Claims, 12 Drawing Sheets

VALVE ASSEMBLY FOR A PROSTHETIC SOCKET

PRIORITY DATA

This application claims the benefit of U.S. Provisional Patent Application Ser. No. 63/070,245, filed Aug. 25, 2020, which is incorporated herein by reference.

BACKGROUND

Prostheses (or prosthetics) are artificial devices that replace body parts (e.g., fingers, hands, arms, legs). Generally, prostheses may be used to replace body parts lost by injury, disease or missing from birth.

There are thousands of individuals with the absence of at least one arm, hand, foot or leg in the United States alone and thousands of new amputees each year. Many of these amputees are fitted with upper or lower extremity prostheses by fitting a prosthetic socket to the residual limb that intimately joins the patient's extremity to the prosthetic device.

DETAILED DESCRIPTION

Figure 1:
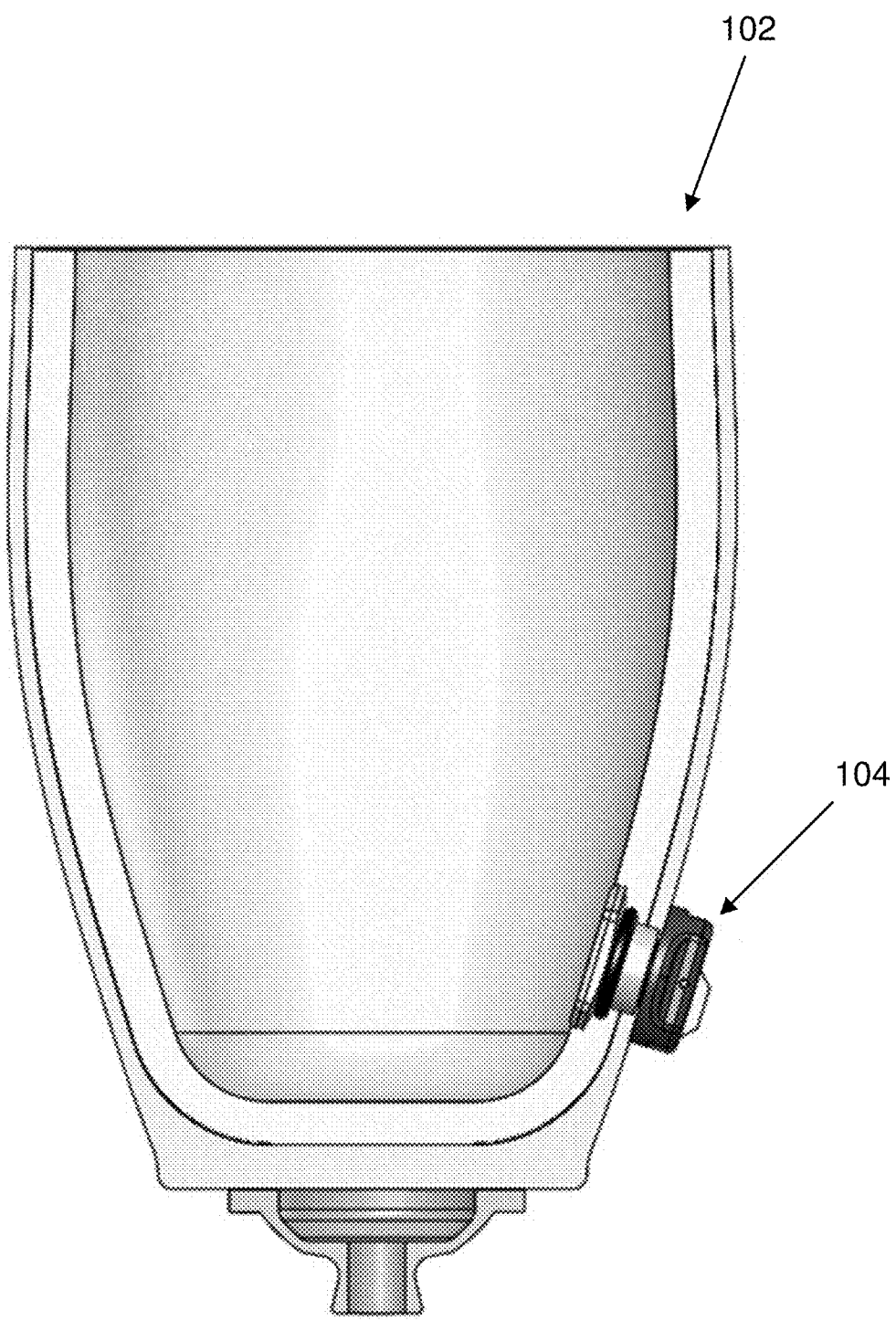
FIG. 1 is a partial cross-sectional view of an example of a prosthetic socket with a valve assembly for air transfer.

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Many prosthetic sockets are constructed from solid and/or composite material that conforms to the residual limb but does not allow air to pass through the prosthetic socket. For example, solid plastics (e.g., polypropylene), other materials (e.g., metal, glass, ceramic, etc.) or various combinations of materials may be used. This solid configuration reduces pressure on the limb by distributing forces across the prosthetic socket when the residual limb is in the prosthetic socket and also helps to maintain tight contact with the residual limb during activity.

One drawback to a cupped type of prosthetic socket design is that air can be trapped between the limb and prosthetic socket when the prosthesis is attached to the remnant limb. An amputee may have difficulties getting a consistent, conforming fit for the residual limb when air becomes trapped in the prosthetic socket. Removal of a residual limb from a prosthetic socket can also be hampered by a sealed prosthetic socket because air can have difficulty flowing into the socket as the limb is being withdrawn and suction (e.g., negative pressure) can occur between the residual limb and prosthetic socket, which may resist removal of the prosthetic socket.

Previous devices on the market have a biased check valve (e.g., spring loaded to only let air pass in one direction) that can let the air out of the prosthetic socket when the remnant limb is seated in the prosthetic socket. The check valve does not let the air back in because the amputee primarily wants to maintain suction (e.g., negative pressure) on the remnant limb. This suction or negative pressure is part of the reason the socket does not simply fall off the arm or leg. In the past, a depressible mechanical switch was the primary mechanism used to open the valve attached to a socket in order to allow the egress of air during socket attachment or the ingress of air during socket removal. The check valve can also block air flow during use of the prosthetic limb.

These previous types of mechanically operated check valves require an amputee to push and hold a button to open the check valve and maintain that mechanical pressure to allow air to leave the socket or to allow air enter back into the socket. More specifically, such depressible switches enable the check valve to be open only when the mechanical switch is actually being pushed. Maintaining the pressure on the button or switch to keep the check valve open while also putting on or removing the prosthetic device can be a significant challenge for an amputee.

The present technology provides a valve assembly that allows for expulsion of air when a remnant limb or residual extremity is inserted into a prosthetic socket of a prosthetic device. Allowing air to escape when the residual extremity is inserted into the prosthetic socket enables the residual extremity to be fully inserted or properly fitted into the prosthetic socket. More specifically, the valve of the present technology allows the air to pass out of the prosthetic socket through the valve assembly so the residual extremity can fit better into the prosthetic socket. Similarly, the present valve can allow air to pass into the prosthetic socket so that the prosthetic socket may be easily removed.

This technology provides a valve assembly and valve latch that can be used to magnetically toggle a valve to enable a remnant limb to better fit into a prosthetic socket. The valve may be a check valve (e.g., spring biased) in one example. In addition, the valve may be manually or electronically driven (e.g., via a solenoid or motor). A position of a valve stem in the valve can be set or located using a stem magnet in the valve stem of the valve or a magnetic ball and one or more magnets in the valve latch. In FIG. 1, an example valve 104 illustrated can be used in a below knee amputation prosthetic socket 102. This valve assembly allows for hands free donning and doffing of a prosthetic device.

As described earlier, prosthetic sockets can be made from strong, thin and/or composite material. This device is minimally intrusive, blends into the socket wall and does not result in any significant decrease in wall strength. The prosthetic socket may be in the form of a plastic cup. The prosthetic socket may alternatively be made of plastics, metals, glass, ceramics, other materials or various combinations of materials. A prosthetic socket may also be used for a wrist, forearm, arm or an above knee amputation.

Figure 2A:
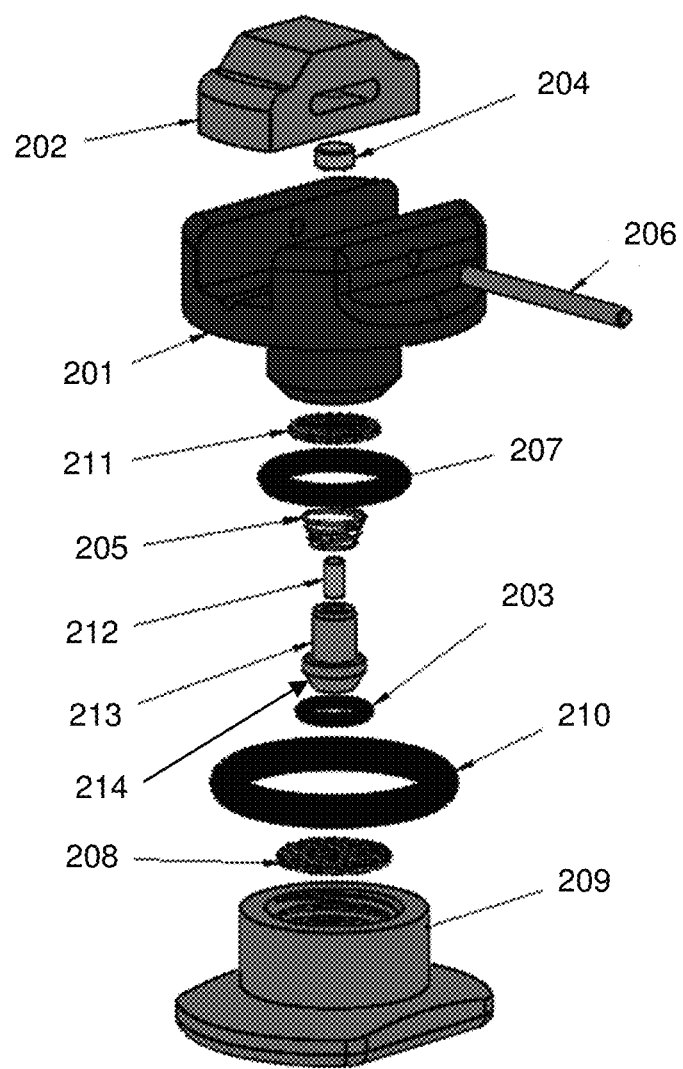
FIG. 2A is an exploded view of an example of a valve assembly with one latch magnet in a valve latch.

FIG. 2A illustrates that the valve mechanics can involve a valve latch 202 and at least one magnet 204 that may allow for hands free donning and doffing of a prosthetic socket. A latch magnet 204 can be associated with (e.g., attached to, embedded in, fixed in or fixed on) the valve latch 202, and a stem magnet 212 may be associated with (e.g., attached to, embedded in or fixed into or on) the valve stem 213. The valve latch 202 may be a sliding latch or a removable latch. The valve stem 213 may also have a valve obstruction that is a tapered valve obstruction 214. The valve stem 213 may also be described as a valve stopper or valve stop. In the illustrated configuration, the stem magnet 212 may be distal from the valve obstruction and valve seat but the stem magnet 212 may have other configurations, such as being attached to the valve obstruction 213 or the stem magnet may be the entire valve stem.

Figure 3A:
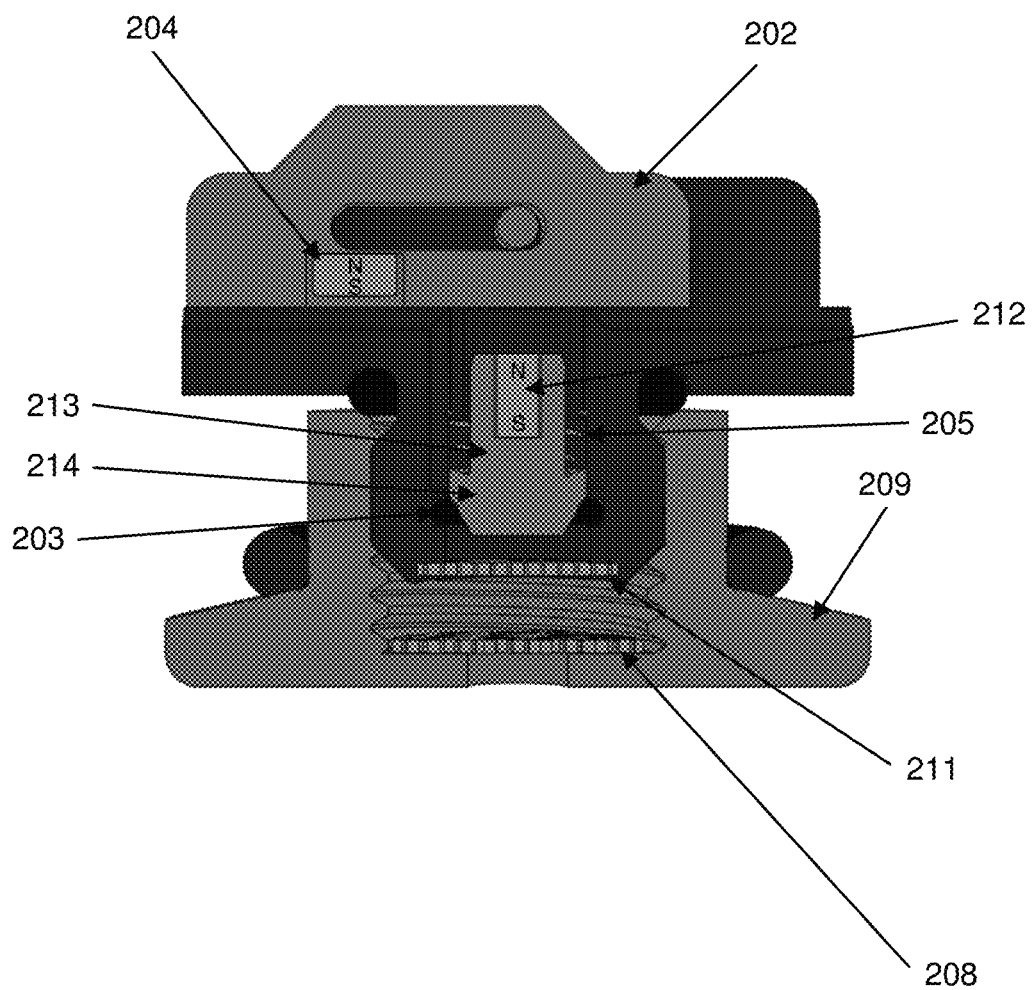
FIG. 3A is a cross-sectional side view of an example of the valve assembly with a valve latch and latch magnet in the closed position.

When the valve latch 202 is in the closed position (as shown in FIG. 3A) the latch magnet 204 is offset from the stem magnet 212 and the valve spring 205 can bias or press the valve stem 213 against the valve O-ring 203. The O-ring 203 may be held in place by the valve seat, and/or the O-ring 203 may form a part of the valve seat or the entire valve seat. Alternatively, the valve seat may be formed in the valve housing using a circular rim (plastic or metal) and the valve stem 213 may rest directly against the valve seat to stop the flow of air. In alternative configurations, the spring 205 may be a coil spring, a leaf spring or a flat spring or any other type of spring or biasing mechanism that could be used to force the valve stem 213 and/or valve obstruction 214 closed. The closed position can prevent air from flowing into the socket but can allow air to escape.

A valve housing 201 can be attached to a prosthetic socket by passing through an opening of the prosthetic socket. The valve housing 201 may be held in place in the prosthetic socket using a valve nut 209. In addition, the valve nut 209 may have a valve nut O-ring 210 to the seal the valve nut 209 against the prosthetic socket, and the valve housing 201 may have a valve housing O-ring 207 to seal the valve housing 201 at the locations where the valve housing meets the valve nut 209.

Figure 2B:
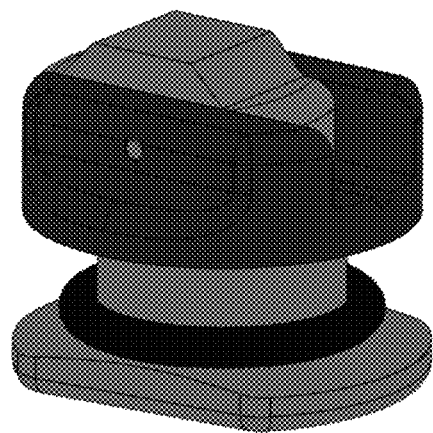
FIG. 2B is a perspective, assembled view of an example of the valve assembly of FIG. 2A with one latch magnet in a valve latch.

The latch 202 may be slidably connected to or attached to the valve housing 201 using a latch pin 206. The valve housing 201 may be threaded or otherwise fastened into a valve nut 209 to hold the valve housing 201 in place through the prosthetic socket (See FIG. 1). A valve nut O-ring 210 may be used to create a seal between the valve nut 209 and an inside wall of the prosthetic socket, and a housing O-ring 207 may be used to create a seal between the valve housing 201 and an outside wall of the prosthetic socket. A valve nut filter 208 may also be included in the assembly to filter dirt, dust and debris from the air that can pass through the valve from the prosthetic socket side. Similarly, a valve housing filter 211 may be provided to filter dirt, dust and debris from air that will enter the valve from outside the prosthetic socket. FIG. 2B is a perspective, assembled view of an example of the valve assembly of FIG. 2A with one latch magnet in a valve latch.

FIG. 3A illustrates a single magnet configuration with the valve latch 202 containing one latch magnet 212 and the valve stem 213 containing a magnet oriented in an opposite polarity to the latch magnet 212. When the valve latch 202 is in the closed position, the latch magnet 212 is moved away from the stem magnet 212 in the valve stem 213, and the valve stem 213 and valve obstruction 214 are pressed against the valve O-ring 203 by the valve spring 203. When the valve stem 213 and/or valve obstruction 214 are against the O-ring 203, the valve assembly still allows the air to flow out when the air pressure in the prosthetic socket exceeds the force created by the spring 213.

Figure 3B:
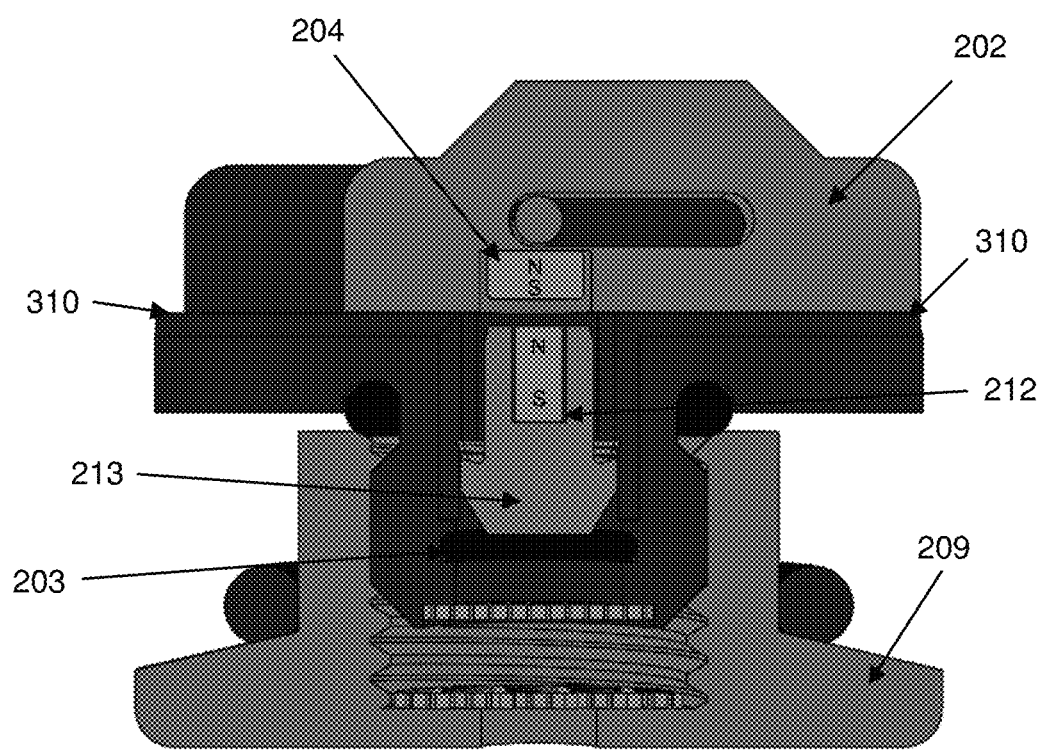
FIG. 3B is a cross-sectional side view of an example of a single latch magnet valve assembly with the valve latch in the open position.

FIG. 3B illustrates valve assembly of FIG. 3A with the valve latch 202 in the open position or the position which opens the valve. This valve latch 202 position places the latch magnet 212 in close proximity with the valve magnet 212 and the magnetic force can be greater than the spring force. More specifically, when the valve latch 202 is in the open position, the opposite poles of the latch magnet 212 and the stem magnet 212 are attractive, and the valve obstruction 214 is pulled away from the valve O-ring 203. The magnetic attractive force between the latch magnet 204 and stem magnet 212 moves the valve stem 213 off the O-ring 203 or valve seat and air is allowed to move through the valve along channels that are an air path 310.

Figure 3C:
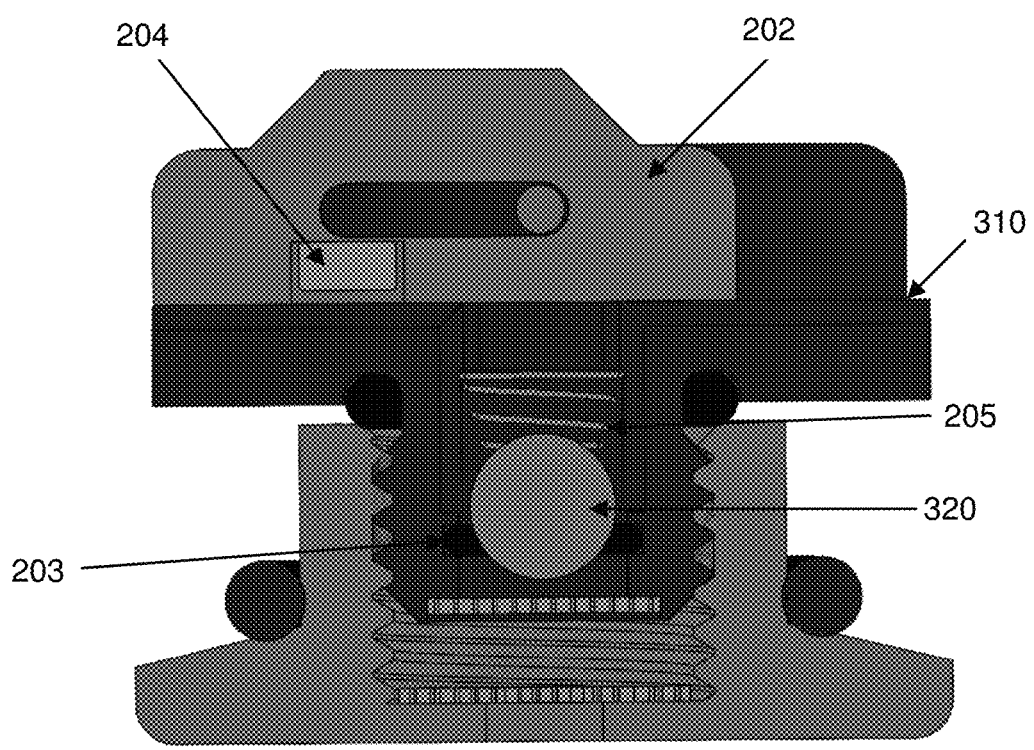
FIG. 3C is a cross-sectional side view of an example of a single latch magnet valve assembly with the valve latch in the closed position and a ball for the valve stem.

FIG. 3C is a cross-sectional side view of an example of a single latch magnet valve assembly with the valve latch 202 in the closed position. In this configuration, the valve may use a valve ball 320 that is magnetized to function as a valve stem. The valve magnet 202 in the open position can attract the valve ball 320 that is magnetized to compress the spring 205 and open the valve. Accordingly, the valve ball 320 is pulled away from the valve O-ring 203 and air is allowed to escape through the valve along the air paths 310. When the valve magnet 202 is in the closed position, the valve ball 320 is biased against the valve O-ring 203 by a spring 205.

While FIG. 3C illustrates a spring biased valve ball configuration, another configuration may use a valve ball without a spring bias. In this configuration, the valve ball 320 may be magnetically attracted and repulsed as illustrated by the two magnet configuration in FIG. 6 which may remove the need for spring biasing.

Figure 4:
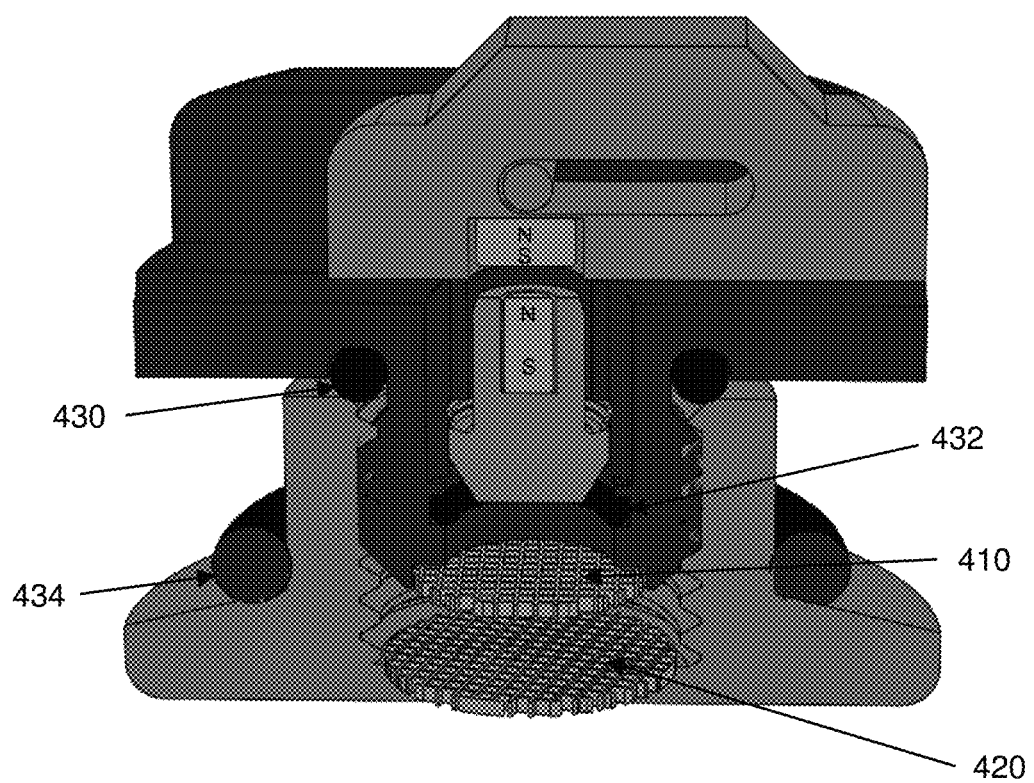
FIG. 4 is a cross-sectional perspective view of an example of a valve assembly with the valve latch in the open position and filter locations.

As illustrated in FIG. 4, one housing filter 410 is provided for the valve housing and one valve nut filter 420 is provided for the valve nut. The filters may inhibit the movement or transmission of particles into the valve mechanics. Also, the valve housing O-ring 430, valve O-ring 432 and valve nut O-ring 434 are used to create an air-tight seal for the valve assembly.

Figure 5:
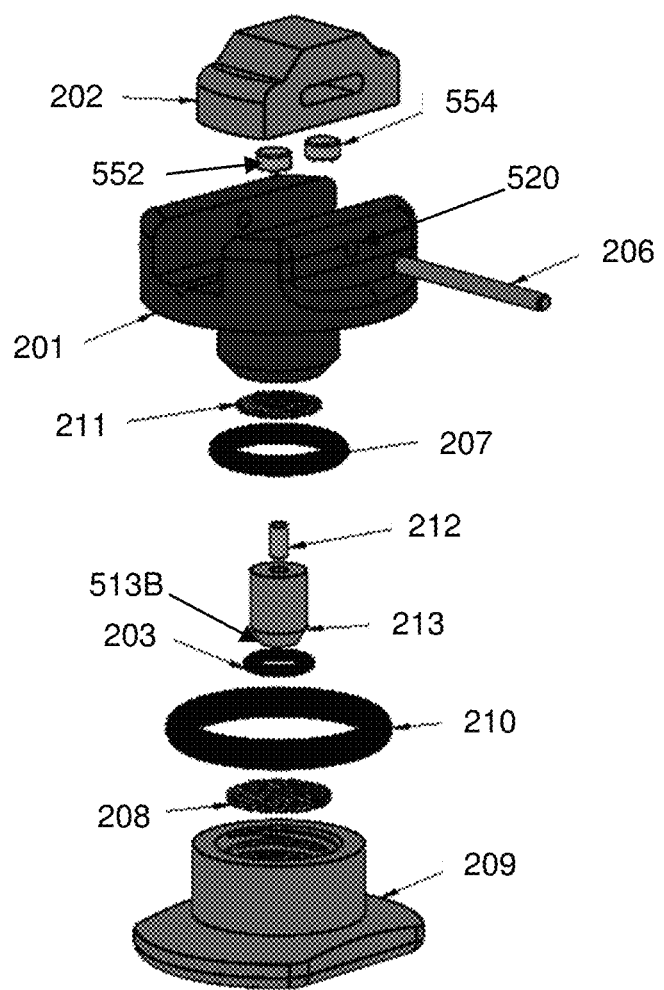
FIG. 5 is an exploded view of an example of the valve assembly with two latch magnets.

FIG. 5 illustrates an exploded view of a valve assembly or valve device with two latch magnets 552, 554. The valve device enables a residual limb to be secured in or removed from a prosthetic socket. In this configuration, one of the magnets may take the place of the spring illustrated in FIGS. 2-3C.

A valve housing 201 can be attached to a prosthetic socket through an opening of the prosthetic socket. The valve housing 201 may be held in place in the prosthetic socket using a valve nut 209. In addition, the valve nut 209 may have a valve nut O-ring 210 to the seal the valve nut 209 against the prosthetic socket, and the valve housing 201 may have a valve housing O-ring 207 to seal the valve housing 201 at the locations where the valve housing 201 meets valve nut 207.

The valve assembly can have a valve stem 213 having a valve obstruction 513B wherein the valve stem 213 can be located in the valve housing 201 and the valve stem 213 may include a stem magnet 212. A valve seat (e.g., a rim) may be provided in the valve housing 201 or valve nut 209 which is configured to receive the valve obstruction 513B.

In an alternative configuration, the valve seat may hold an O-ring 203 in the valve housing 201 to receive the valve stem 213 and the valve obstruction 513B. For example, the valve seat may include one or more flanges, collars or rims to hold the O-ring 203 in place, and the O-ring 203 may come in contact with the valve stem 213 or valve obstruction 513B rather than the valve seat.

In other configurations, the valve obstruction 513B may be a disk, a cone, a ball or a square gate on an end of the valve stem 213. The stem magnet 212 may be on an opposite end of the valve stem 213 as compared to the valve obstruction 513B of the valve stem 213, and the valve stem 213 shape may substantially be a cylinder. Alternatively, the valve stem 213 shape may be rectangular, square or another shape.

A valve latch 202 or switch can be set in the open position and the valve may remain open (e.g., magnetically held open). As a result, the user or amputee can use both hands to remove the prosthetic socket while air flows through the valve. When the valve latch 202 or switch is moved the other way to the off position and the valve is in the closed position (e.g., magnetically held closed) then an amputee can use both hands to put on the prosthetic device.

The valve latch 201 may be movably, slidably, rotatably, or removably mounted with respect to the valve housing 201 and the valve stem 213. In one example, a pin 206 may be used hold the valve latch 202 in place with respect to the valve housing 201 by passing through an aperture 520 of the valve latch 202, and the pin 206 may enable the valve latch 202 to translate in a direction substantially orthogonal to a lengthwise axis of the valve stem 213. In another configuration, the valve latch may be more than one valve latch (e.g., two removable valve latches) and/or the valve latch(es) may translate at an angle with respect to the longitudinal axis of the valve stem 213 or valve magnet 212 (e.g., translate in a V shape).

The valve assembly may include a first latch magnet 552 with a first polarity, wherein the first latch magnet 552 may be attached to the valve latch 202. In addition, the valve assembly may include a second latch magnet 554 with a reversed polarity as compared to the first polarity of the first latch magnet 552 and a polarity of the stem magnet 212. The second latch magnet 554 can be attached to the valve latch 202 and the valve latch 202 is configured to move the first latch magnet 552 and the second latch magnet 554 with respect to stem magnet 212 or valve stem 213. A first position of the valve latch 202 may magnetically hold the valve stem 213 in an open position using the first latch magnet 552 and the stem magnet 212. In contrast, a second position of the valve latch 202 may magnetically hold the valve stem 213 in a closed position using the second latch 554 magnet and the stem magnet 212.

More specifically, this valve can be activated by the latch magnets 552, 554 as the latch magnets 552, 554 magnetically interact with the stem magnet 212. The first latch magnet 552 may have an opposite north and south polarity as compared to the second latch magnet 554. The ordering of the magnets in the latch could be in any order depending on which direction or spatial orientation the latch moves. In an example, one latch magnet may be oriented in a first polarity to magnetically push the valve stem 213 and/or valve obstruction 513B against the O-ring and close off the air flow. When the switch is moved to a second position, then a second latch magnet with an opposite polarity from the first latch magnet or a second polarity may magnetically open the valve stem 213 in the valve.

The valve latch 202 may have a number of configurations. In a first configuration, the valve latch 202 may move in a direction that is a direction transverse to a lengthwise axis of the stem magnet 212 or valve stem 213. In a rotational configuration example, the valve latch 202 may move in a rotational direction (e.g., around or perpendicular) with respect to the lengthwise axis of the stem magnet 212.

Alternatively, the valve latch 202 may move in a direction aligned with the lengthwise axis of the valve stem (e.g., up and down). In yet another configuration, the valve latch may move at an acute angle with respect to the lengthwise axis of the valve stem (e.g., in a V shape in a conical path or in a V shape in an orthogonal plane as compared to the longitudinal axis of the stem magnet 212).

In one example of the use of the magnets, the valve latch 202 can bring a pole of the first latch magnet (e.g., North pole) into proximity with an opposite pole of the stem magnet 212 (e.g., South pole) to magnetically attract the stem magnet 212 and hold the valve stem 213 in an open position. The valve latch 202 may also move a pole of the second latch magnet (e.g., South Pole) into proximity with a matching pole of the stem magnet (e.g., South Pole) to magnetically repel the stem magnet and hold the valve stem in a closed position. These magnetic pole examples can also be inverted. Thus, the positioning of the valve latch may enable a free flow of air (i.e., minimally impeded) from an interior of the prosthetic socket to an exterior of the prosthetic socket or the air may be blocked (unless overcome by air pressure from the prosthetic socket side) depending on a position of the valve latch.

Figure 6:
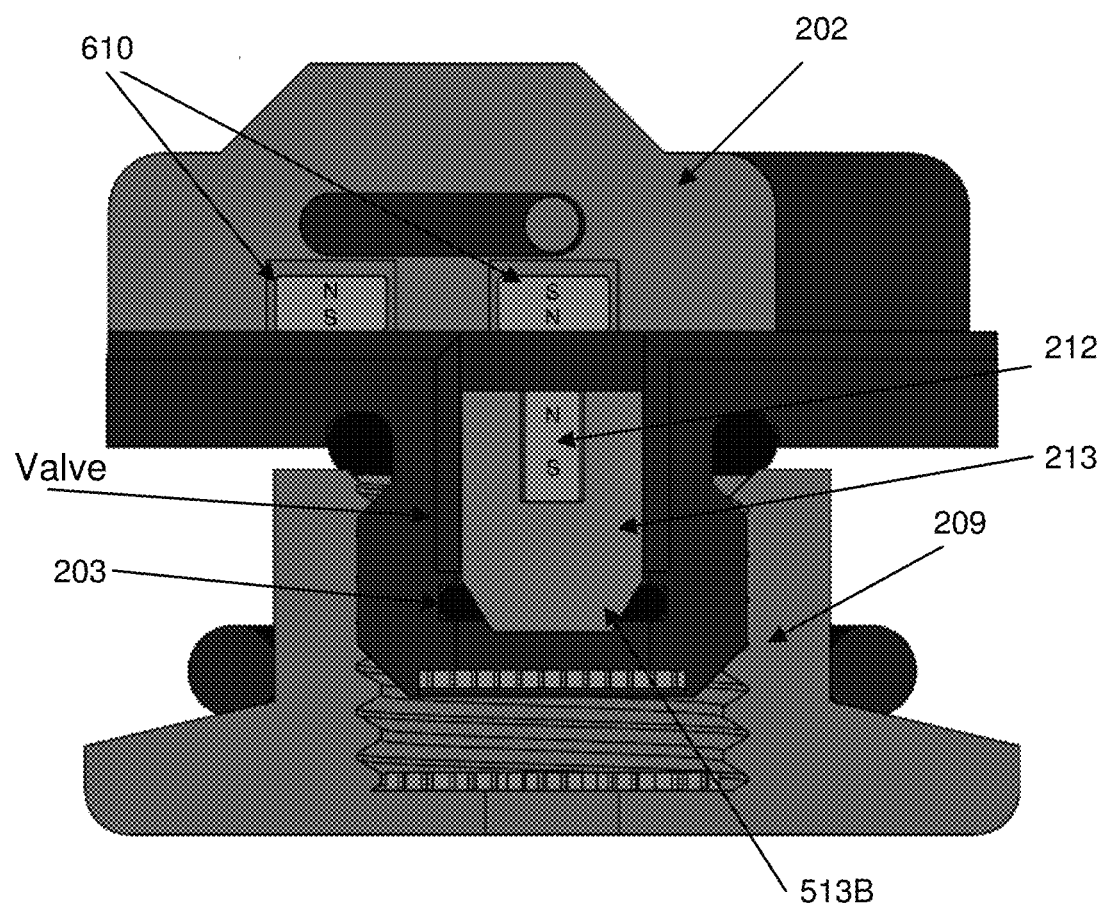
FIG. 6 is a cross-sectional side view of an example of a double latch magnet in a valve assembly with the valve latch in the closed position.

FIG. 6 illustrates a double magnet configuration with the valve latch 202 containing two magnets 610 arranged in opposite polarities. When the valve latch 202 is in the closed position, as shown, the magnetic poles of the first latch magnet and the stem magnet are repulsive and the valve magnet 212 and valve stem 213 may be pressed against the valve O-ring 203. In the closed position, when the force of the air pressure created by inserting a remnant limb into a prosthetic socket overcomes the magnetic force between the magnets, then air may flow out of the prosthetic socket.

The two-magnet 610 configuration is useful because the two-magnet configuration creates only a limited amount of part movement or play in the valve assembly due to the significant force of the magnetic repulsion or attraction. For example, the magnets may be neodymium magnets. Further, the latch magnets or stem magnet 212 may be a magnet 1/16 of an inch by 1/8 of an inch in size or another usable size dimension.

The latch magnets 610 are located in or on the latch 202 so that the correct magnet is moved into place depending on whether the user or amputee wants to move the valve stem 212 and valve obstruction 513B in or out (e.g., open or close the valve). Magnetic force follows the inverse square law. So, a latch magnet 610 that is very close to the stem magnet 213 creates a strong magnetic interaction with the stem magnet 212 but when the latch magnet 610 is farther away from the stem magnet 212, then the interaction between the magnets is significantly weaker as defined by the distance between the magnets. The valve latch 202 can move the latch magnets with defined polarities closer and farther away from the stem magnet 212 (that has a stem magnet polarity) to move the valve stem 213.

The valve latch illustrated in FIG. 6 translates with respect to the valve housing. The translation of the valve latch may be orthogonal to or perpendicular (not shown) to the axis of the valve stem.

As discussed before, a rotational device may rotate latch magnets closer to or farther from the stem magnet using a rotational wheel. When a rotational valve latch rotates a latch magnet close to the stem magnet, the desired magnetic interaction may occur to move the valve stem and open or close the valve. For example, the rotational wheel may be a scroll wheel. The axis of the scroll wheel may be parallel with the axis of the valve stem axis in a carousel orientation (e.g., the rotational wheel axis has a parallel axis to the valve stem axis or the same axis). Alternatively, the scroll wheel may rotate on an axis orthogonal to the axis of the valve stem and valve magnet (e.g., like a Ferris wheel with respect to the stem magnet).

In yet another configuration, the latch magnets may be translated closer to and farther from a magnetic pole of the stem magnet. In the case of using one latch magnet and spring, a latch magnet may be moved to a distant position to allow the valve to be closed by a spring, and the latch position that places a latch magnet in a position near the stem magnet may open the valve using magnetic attraction.

In another example configuration, a single magnet with two poles may spin around an axis that is orthogonal to a lengthwise axis of the stem magnet. More specifically, the magnet may turn around an axis that divides the magnet in half and each pole is in one half. As a result, the poles of the magnet may be spun around the axis and used to magnetically open or close the valve stem.

In order to move the valve stem 213 and stem magnet 212 between the open and closed position, the magnets may be in a valve latch 202 or moving body (e.g., a carriage) that brings the latch magnets closer to and moves the latch magnets farther way from the stem magnet. The valve latch 202 can position the latch magnets closer to or farther way from the stem magnet 212 and valve stem 213 with a moving valve latch 202 or moving latch piece. The valve latch can translate the magnets perpendicularly or rotationally with respect to the magnetic pole of the valve magnet. Alternatively, the valve latch 202 can move the latch magnet(s) in line with the lengthwise axis of the stem magnet. The latch can move the latch magnets into or away from the magnetic field or flux lines of the stem magnet. Thus, in the two-latch magnet configuration, magnetic force can be used to move and hold the valve (e.g., the valve stem and valve magnet) in the open position or the closed position.

Figure 7A:
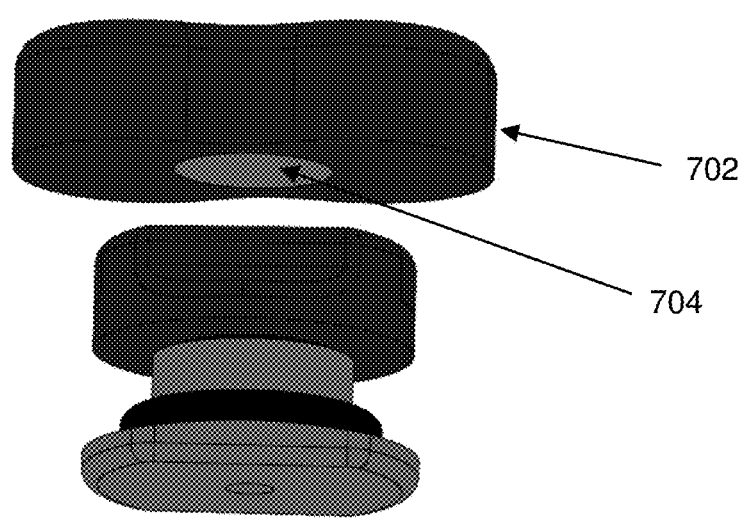
FIG. 7A illustrates an example of a removable magnetic valve latch.

FIG. 7A illustrates a removable magnetic valve latch configuration. This may also be called a remote latch configuration. The valve latch may be a removable magnetic valve latch 702 with a removable latch magnet 704 that an amputee or another user places in proximity over the valve stem in order to open or close the valve magnetically. For example, the removable magnet valve latch may not be attached to the valve housing but may instead be a ring on an amputee's hand with a magnet in or on the ring. In another example, the removable magnetic valve latch may be a latch housing that is attached to a keychain owned by the amputee. In further examples, the valve latch may be shaped as a block, round puck, an animal, or a fantasy character. In another configuration, the removable magnetic valve latch 702 may be loosely attached to the prosthetic socket or the valve housing with a chain, plastic zip tie or another length of material used as a fastener.

Figure 7B:
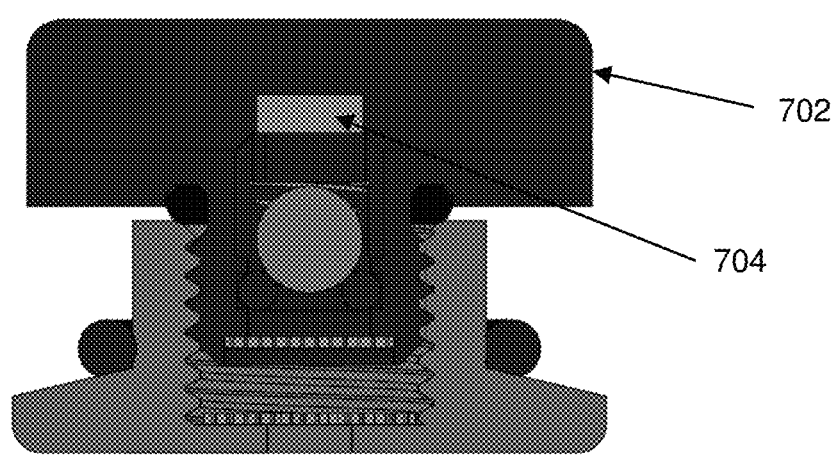
FIG. 7B illustrates an example cross-sectional view of the removable magnetic valve latch.

FIG. 7B illustrates a cross-sectional view of the removable magnetic valve latch configuration, when the removable magnetic valve latch 702 and removable latch magnet 704 are near to the ball valve.

Figure 8:
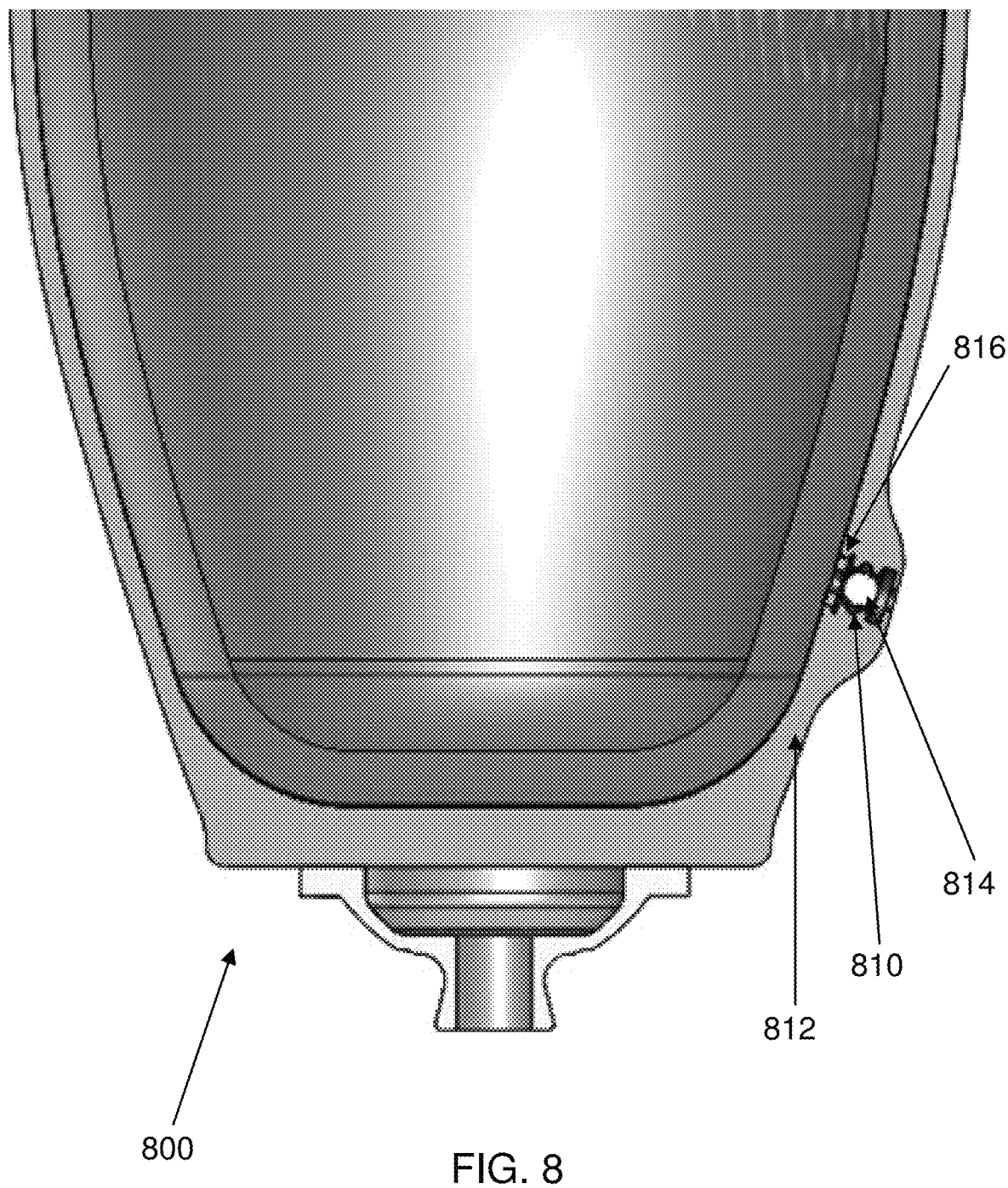
FIG. 8 illustrates an example of the magnetic latch assembly with elements of the latch housing formed into the prosthetic socket.

FIG. 8 illustrates an example of the magnetic latch assembly where a housing structure of the magnetic latch is formed into the prosthetic socket 800 using 3D printing or additive manufacturing. FIG. 8 illustrates the example use of a valve ball 814 as the valve piece or valve stem. In this configuration, the valve housing may be formed into a wall 812 of the prosthetic socket. The valve housing may be a valve chamber 810 or valve channel that provides an air passage through the prosthetic socket. The valve chamber 810 may provide the valve housing for the valve structures described earlier. The structures inside the valve chamber 810 may be similar to valve assembly elements in FIG. 2A or FIG. 3C. However, some parts such as a valve nut 209, valve nut O-ring 210, and valve nut filter 208 and similar parts may not be needed in this configuration. The inner structures of the valve such as the valve ball, valve magnet, spring and other elements may be held in place in the prosthetic socket by the valve chamber 810, an inner gasket 816 and an inner filter.

The described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A valve device to enable a remnant limb to be placed in a prosthetic socket, comprising:
   a valve chamber formed into a wall of the prosthetic socket to form an air passage through the prosthetic socket;
   a valve ball forming a valve obstruction, wherein the valve ball is in the valve chamber and the valve ball is magnetized;
   a valve seat which is configured to receive the valve obstruction;
   a valve latch, movable with respect to the valve chamber and the valve obstruction; and
   a first latch magnet with a first polarity, wherein the first latch magnet is attached to the valve latch, wherein the valve latch is configured to move the first latch magnet with respect to the valve ball to provide an open and closed position.

2. The valve device of claim 1, a second latch magnet, with a reversed polarity as compared to the first polarity of the first latch magnet, wherein the second latch magnet is attached to the valve latch.

3. The valve device of claim 2, wherein the valve latch is configured to move the first latch magnet and the second latch magnet with respect to the valve ball.

4. The valve device of claim 2, wherein a first position of the valve latch magnetically sets the valve ball in an open position using the first latch magnet and the valve ball, and a second position of the valve latch magnetically sets the valve ball in a closed position using the second latch magnet.

5. The valve device of claim 1, wherein the valve latch moves in a direction that is at least one of: a direction transverse to a lengthwise axis of the valve device, a rotational direction with respect to the lengthwise axis of the valve device, a direction aligned with the lengthwise axis of the valve device, or a direction at an angle with respect to the lengthwise axis of the valve device.

6. The valve device of claim 1, further comprising a valve gasket to retain the valve ball, valve seat, valve latch, and first latch magnet in the valve chamber.

7. The valve device of claim 1, further comprising a spring to bias the valve ball in a closed position.

8. A valve device to enable a remnant limb to be secured in a prosthetic socket, comprising:
 a valve housing associated with an air opening of the prosthetic socket;
 a valve stem having a valve obstruction, wherein the valve stem is in the valve housing and the valve stem includes a stem magnet;
 a valve seat which is configured to receive the valve obstruction;
 a valve latch, movable with respect to the valve housing and the valve stem;
 a first latch magnet with a first polarity, wherein the first latch magnet is attached to the valve latch; and
 a second latch magnet, with a reversed polarity as compared to the first polarity and stem magnet, wherein the second latch magnet is attached to the valve latch and the valve latch is configured to move the first latch magnet and the second latch magnet with respect to stem magnet, and a first position of the valve latch magnetically sets the valve stem in an open position using the first latch magnet and the stem magnet, and a second position of the valve latch magnetically sets the valve stem in a closed position using the second latch magnet and the stem magnet.

9. The valve device of claim 8, wherein the valve latch moves in a direction that is at least one of: a direction transverse to a lengthwise axis of the stem magnet or valve stem, a rotational direction with respect to the stem magnet, a direction aligned with the lengthwise axis of the valve stem, or a direction at an angle with respect to the lengthwise axis of the valve stem.

10. The valve device of claim 8, wherein a pole of the first latch magnet is brought into proximity with an opposite pole of the stem magnet to magnetically attract the stem magnet and hold the valve stem in an open position.

11. The valve device of claim 8, wherein a pole of the second latch magnet is brought into proximity with a matching pole of the stem magnet to magnetically repel the stem magnet and hold the valve stem in a closed position.

12. The valve device of claim 8, wherein the valve obstruction is a disk, a cone, a ball, magnetic ball or a gate on an end of the valve stem.

13. The valve device of claim 8, further comprising a valve nut coupled to the valve housing to fasten the valve device through a wall of the prosthetic socket.

14. A valve device to enable a remnant limb to be secured in a prosthetic socket, comprising:
 a valve housing;
 a valve stem having a valve obstruction, wherein the valve stem is in the valve housing and the valve stem has a stem magnet;
 a valve seat formed into the valve housing to receive the valve obstruction;
 a spring to bias the valve stem and valve obstruction against the valve seat; and
 a valve latch, movable with respect to the valve housing and valve stem, the valve latch having a latch magnet, wherein a first position of the valve latch enables the latch magnet and stem magnet to magnetically hold the valve stem in an open position and a second position of the valve latch enables the valve stem and valve obstruction to be in a closed position as biased by the spring.

15. The valve device of claim 14, wherein the valve latch moves in a direction that is at least one of: a direction transverse to a lengthwise axis of the stem magnet or valve stem, rotationally with respect to a lengthwise axis of the stem magnet or a direction aligned with the lengthwise axis of the valve stem.

16. The valve device of claim 14, wherein a first pole of the latch magnet is brought into proximity with an opposite pole of the stem magnet to magnetically attract the stem magnet and hold the valve stem open.

17. The valve device of claim 14, wherein the valve latch is configured to travel orthogonally with respect to a longitudinal axis of the valve stem.

18. The valve device of claim 14, wherein the stem magnet is distal to the valve obstruction in the valve stem.

19. The valve device of claim 14, wherein positioning of the valve latch enables a flow of air to be minimally impeded from an interior of the prosthetic socket to an exterior of the prosthetic socket based in part on a position of the valve latch.

20. The valve device of claim 14, wherein the spring is at least one of: a coil spring, a leaf spring or flat spring.

21. The valve device of claim 14, wherein the valve seat is at least one of: an O-ring or a circular rim formed in the valve housing.

* * * * *